(12) United States Patent
Eyal-Bickels et al.

(10) Patent No.: US 6,849,046 B1
(45) Date of Patent: Feb. 1, 2005

(54) SYSTEM AND METHOD FOR DETECTING THE STATE OF HYDRATION OF A LIVING SPECIMEN

(76) Inventors: Elazar Eyal-Bickels, 26 Michal St., Tel-Aviv (IL), 61640; Shulamit Margaliot, 1 Rabbi Yossi Street, Bnei-Brak (IL), 51405

(*) Notice: Subject to any disclaimer, the term of this patent is extended or adjusted under 35 U.S.C. 154(b) by 105 days.

(21) Appl. No.: 10/088,938
(22) PCT Filed: Sep. 21, 2000
(86) PCT No.: PCT/IL00/00585
§ 371 (c)(1), (2), (4) Date: Mar. 21, 2002
(87) PCT Pub. No.: WO01/21068
PCT Pub. Date: Mar. 29, 2001

(30) Foreign Application Priority Data

Sep. 23, 1999 (IL) .................................. 132027

(51) Int. Cl.[7] .............................................. A61B 5/00
(52) U.S. Cl. .................. 600/309; 600/310; 600/306; 600/430
(58) Field of Search ............................... 600/309–310, 600/306, 430

(56) References Cited

U.S. PATENT DOCUMENTS 4,364,008 A * 12/1982 Jacques ...................... 600/306
4,488,559 A    12/1984 Iskander
5,767,685 A     6/1998 Walker

FOREIGN PATENT DOCUMENTS

WO    WO 83/03746    11/1983
WO    WO 92/13485     8/1992

OTHER PUBLICATIONS

Lozano–Nieto,A.; "Impedance Ratio in Bioelectrical Impedance Measurementsfor Body Fluid Shift Determination;" Apr. 9–10, 1998; Proceedings of the IEEE Annual Northeast Bioengineering Conference(Cat. No. 98CH36210); Hershey, PA, USA; pp. 24–25; XP002157035.

* cited by examiner

Primary Examiner—Max F. Hindenburg
Assistant Examiner—Matthew Kremer
(74) Attorney, Agent, or Firm—Fenster & Company

(57) ABSTRACT

The invention provides a system (2) for non-invasive detection of the state of hydration in a living specimen, the system including an RF generator/transmitter (416) for emitting RF radiation signals and for transmitting the radiation signals through a tissue of a living specimen; an RF receiver (8) for receiving RF signals transmitted through the tissue, and for feeding the signals to a processor (10) for comparison of relative attenuation of RF frequencies passing through the tissue with a reference attenuation ratio signal, and an indicator unit (12) for providing an output signal representative of the water content level of the tissue. A method for non-invasive detection of the state of hydration in a living specimen is also described and claimed.

22 Claims, 1 Drawing Sheet

SYSTEM AND METHOD FOR DETECTING THE STATE OF HYDRATION OF A LIVING SPECIMEN

RELATED APPLICATIONS

This application is a U.S. national filing of PCT Application No. PCT/IL00/00585, filed Sep. 21, 2000.

FIELD OF THE INVENTION

The present invention relates to a system and a method for non-invasively detecting the state of hydration of a living specimen.

The term "living specimen" as used herein is intended to define living tissue of a human, an animal or a plant.

BACKGROUND OF THE INVENTION

The hydration state is important to all living organisms, Dehydration is a well-known phenomenon, in which a living body loses moisture to an excessive degree. Normally, the loss of body water will invoke thirst and thus induce drinking. However, tinder special conditions, such as the extremely hot and dry ambient atmosphere found in the, desert, the sensation of thirst might not be strong enough and the drinking rate thus induced may not be sufficient. The possible resulting dehydration can, in some cases, turn out to be fatal. In addition, over-hydration may occur during dialysis treatment of kidney diseases and may have serious consequences.

DISCLOSURE OF THE INVENTION

It is therefore a broad object of the present invention to provide a system and method for non-invasively detecting the state of hydration in a living specimen and to provide a warning signal upon the detection of a deviation from the normal state.

The invention provides a system for non-invasive detection of the state of hydration in a living specimen, said system comprising an RF generator/transmitter for emitting RF radiation signals and for transmitting said radiation signals through a tissue of a living specimen; a processor, and an indicator unit for providing an output signal representative of the water content level of said tissue; characterized in that said processor receives signals from said receiver and compares the intensity of the signals passing through said tissue with that of a reference signal, indicating the state of hydration of said living tissue.

The invention further provides a method for non-invasive detection of the state of hydration in a living specimen, said method comprising providing a system for non-invasive detection of the state of hydration in a living specimen, said system comprising an RF generator/transmitter for emitting RF radiation signals and for transmitting said radiation signals through a tissue of a living specimen; a processor, and an indicator unit for providing an output signal representative of the water content level of said tissue; characterized in that said processor receives signals from said receiver and compares the intensity of the signals passing through said tissue with that of a reference signal, indicating the state of hydration of said living tissue; introducing into said processor a reference signal indicative of the normal water content level in the tissue of said specimen; passing RF signals through said tissue and feeding said signals to said processor; receiving signals passed through said tissue and comparing the intensity of the RF signals passing through said tissue with said reference signal, and providing an output signal indicative of the water content level of said tissue.

BRIEF DESCRIPTION OF THE DRAWINGS

The invention will now be described in connection with certain preferred embodiments with reference to the following illustrative figure, so that it may be more fully understood.

With specific reference now to the figure in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawing making apparent to those skilled in the art how the several forms of the invention may be embodied in practice.

In the drawing:

FIG. 1 is a block diagram of the system according to the present invention for detecting dehydration of a living body.

DETAILED DESCRIPTION

Figure 1:
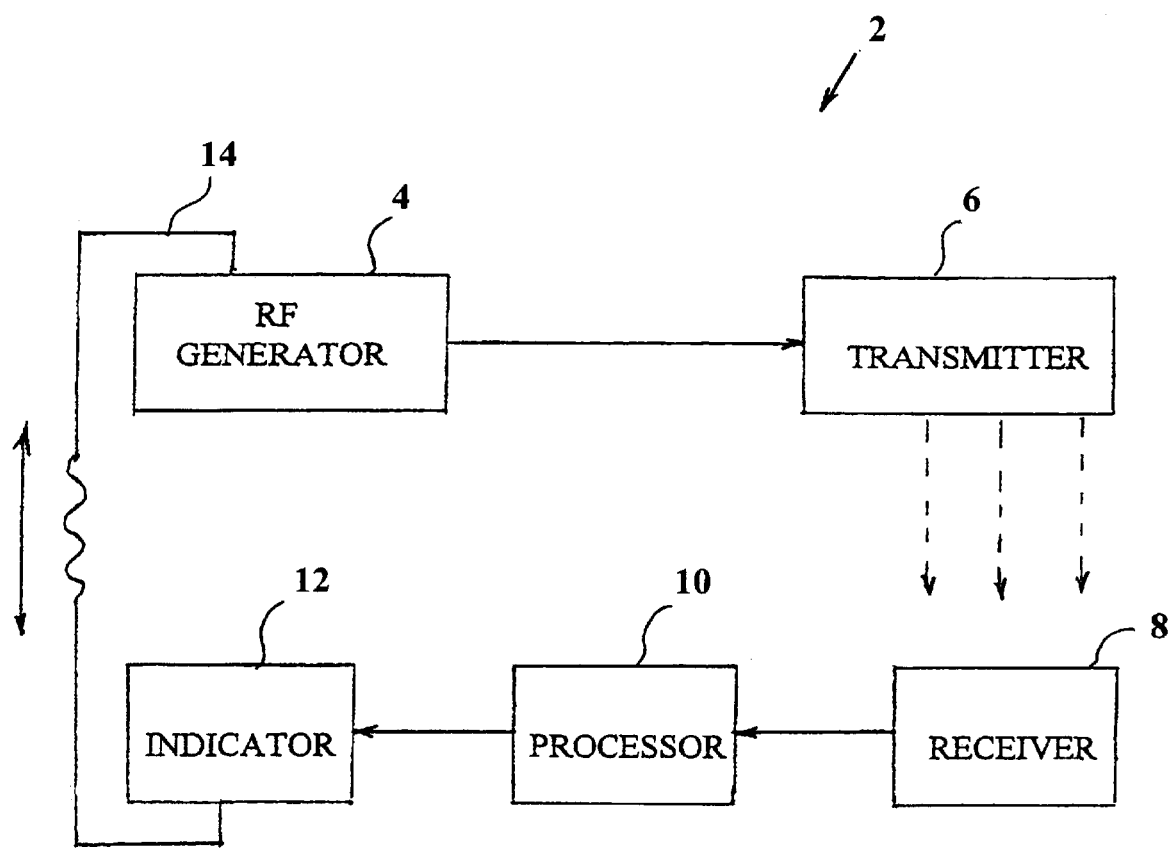

One of the most prominent electrical properties of the tissue of a living body which is dependent upon its water content is its attenuation coefficient at electromagnetic radiation in the radio frequency (RF) region, when such radiation is passed through the tissue. The absorption of RF radiation by body tissue at low RF frequencies (between 10 kHz and 2 GHz) involves induction of ionic motion of the ions dissolved in the body water. At high RF frequencies (above 2 GHz and up to 300 GHz), the process by which RF energy is absorbed by the body water, is by induction of rotational excitation of the water molecules themselves. It is this last property of variation in mode of interaction due to frequency variations that constitutes the basis for a non-invasive method for detection of the water content level of a living body.

Seen in FIG. 1 is a system 2 which includes an RF generator 4 and a transmitter 6 for transmitting the generated RF radiation signal, a receiver 8 for receiving the signal passing through a tissue or member of a living body, a processor 10 for processing the signal received by receiver 8, and an indicator unit 12 for displaying or otherwise providing an output signal, e.g., an alarm, indicative of the degree of dehydration of the body.

The method consists of operating the RF generator 4 and transmitter 6 at RP frequencies, and operating an RF receiver at the same frequencies. A set of RF radiation signals is transmitted from transmitter 6 to receiver 8 via an appropriate member of a living body, such as a hand, foot, etc., and the intensity of the set of attenuated received signals at various RF frequencies is compared in processor 10 to the intensity of a set of reference signals obtained for the same member of the body of the same user when the user is subjected to standard conditions of normal body water content. Alternatively, the reference signal may be predetermined and preset in processor 10, in accordance with known average body water content levels. When the intensity of the received signals is significantly different from that of the reference signal, an output signal, consisting of an alarm, beeper or warning light, a vibration alarm, or a combination thereof, is activated, thus drawing the user's attention to the fact that his body is becoming dehydrated or over-hydrated. Alternatively, the hydration state may continuously be displayed on any kind of numerical or analog display.

According to a preferred embodiment of the present invention, the frequencies used are 2.45 GHz and 40.68 MHz, and system 2, including transmitter 4, receiver 6 and indicator unit 12, is attached to the user's wrist by any suitable, adjustable means 14, made of a non-conductive material.

It should be noted that using more than two frequencies improves accuracy and reliability, and the above-described embodiment has been presented for reasons of simplicity only.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for non-invasive detection of the state of hydration in a living specimen, said system comprising:

an RF generator/transmitter for emitting RF radiation signals at a plurality of frequencies and for transmitting said radiation signals through a tissue of a living specimen;

a receiver adapted to receive RF radiation Signals passing through the living specimen at the plurality of frequencies;

a processor; and an indicator unit for providing an output signal representative of a hydration state of said tissue;

wherein said processor receives signals from said receiver and compares the intensity of the transmitted RF signals, at the plurality of frequencies, passing through said tissue with that of at least one reference value, indicating the state of hydration of said living tissue.

2. The system as claimed in claim 1, wherein said generator/transmitter emits RF radiation at frequencies of between 10 kHz and 300 GHz.

3. The system as claimed in claim 1, wherein said indicator unit provides an audible, visual or palpating output signal.

4. The system as claimed in claim 1, further including means for attaching said system to a wrist the user's body.

5. The system as claimed in claim 1, wherein the plurality of frequencies include at least one low frequency at which RF energy causes induction of ionic motion of ions dissolved in the body water.

6. The system as claimed in claim 5, wherein the plurality of frequencies include a frequency around 40 MHz.

7. The system as claimed in claim 5, wherein the plurality of frequencies include at least one high frequency at which RE energy is absorbed by body water by rotational excitation of water molecules.

8. The system as claimed in claim 7, wherein the plurality of frequencies include a frequency around 2.4 GHz.

9. The system as claimed in claim 1, wherein the plurality of frequencies include more than two frequencies.

10. The system as claimed in claim 1, wherein the indicator unit provides a warning signal when the living specimen is dehydrated.

11. The system as claimed in claim 1, wherein the indicator unit provides a warning signal when the living specimen is dehydrated.

12. The system as claimed in claim 1, wherein the processor is adapted to store the intensity of the transmitted RF signals, at the plurality of frequencies, passing through said tissue, under standard conditions, for use as the at least one reference value.

13. The system as claimed in claim 1, wherein the processor is preset with the at least one reference values, in accordance with known average body water content levels.

14. The system as claimed in claim 1, wherein the transmitter and receiver have separate ports leading to the living specimen.

15. The system as claimed in claim 1, wherein said at least one reference value comprises at least one attenuation ratio.

16. The system as claimed in claim 1, wherein said receiver is adapted to receive a signal transmitted through said tissue.

17. A method for non-invasive detection of the state of hydration in a living specimen, said method comprising:

introducing into processor at least one reference signals;

passing RF signals, at a plurality of frequencies, through said tissue;

feeding said signals passed through the tissue to said processor;

comparing the intensity of the RF signals passed through said tissue with at least one said reference signal; and providing an output signal indicative of a hydration state of the living specimen responsive to the comparison.

18. The method as claimed in claim 17, wherein said at least one reference signal is obtained by passing RF signals through the same tissue of the same user when subjected to standard hydration conditions.

19. The method as claimed in claim 17, wherein said output signal is an audible, visual or palpating signal.

20. The method as claimed in claim 17, wherein said RF signals are passed through the tissue at the same frequencies as frequencies of said reference signals.

21. The method as claimed in claim 17, wherein passing RF signals through the tissue comprises passing through a hand.

22. The method as claimed in claim 17, wherein passing RF signals through the tissue comprises transmitting air signals from the transmitter to the receiver via a member of a living body.

* * * * *